United States Patent [19]

Drent et al.

[11] Patent Number: 5,436,356
[45] Date of Patent: Jul. 25, 1995

[54] CARBONYLATION PROCESS

[75] Inventors: Eit Drent; Dennis H. L. Pello; Melis Hasselaar, all of Amsterdam, Netherlands

[73] Assignee: Shell Oil Company, Houston, Tex.

[21] Appl. No.: 183,009

[22] Filed: Jan. 14, 1994

[30] Foreign Application Priority Data

Feb. 9, 1993 [EP] European Pat. Off. ............ 93200360

[51] Int. Cl.$^6$ .................................................. C07C 5/10
[52] U.S. Cl. ..................................... 554/129; 554/128; 560/175; 560/204; 560/207; 562/517; 562/522; 564/132; 568/480
[58] Field of Search ................. 554/129, 128; 560/204, 560/207, 175; 562/522, 517; 564/132; 568/480

[56] References Cited

U.S. PATENT DOCUMENTS

| | | | |
|---|---|---|---|
| 4,172,087 | 10/1979 | Knifton | 554/129 |
| 4,645,855 | 2/1987 | Reuvers et al. | 560/204 |
| 4,849,542 | 7/1989 | Drent | 560/175 |

FOREIGN PATENT DOCUMENTS

| | | |
|---|---|---|
| 055875 | 7/1982 | European Pat. Off. |
| 0055875A1 | 7/1982 | European Pat. Off. |
| 0143911A1 | 6/1985 | European Pat. Off. |
| 0274795A2 | 7/1988 | European Pat. Off. |
| 0495547A2 | 7/1992 | European Pat. Off. |
| 1127965 | 9/1968 | United Kingdom. |
| 2058074A | 4/1981 | United Kingdom. |
| 2185740A | 7/1987 | United Kingdom. |

*Primary Examiner*—José G. Dees
*Assistant Examiner*—Deborah D. Carr

[57] ABSTRACT

A process for the carbonylation of ethylenically unsaturated compounds by reaction with carbon monoxide and a co-reactant in the presence of a substantially non-acidic catalyst system based on a palladium compound and a bidentate ligand of the formula $$R_1R_2M_1RM_2R_3R_4$$

in which $M_1$ and $M_2$ may be phosphorus, arsenic or antimony atom, R is a bivalent organic bridging group, $R_1$, $R_2$, $R_3$ and $R_4$ are independently substituted or non-substituted aliphatic groups, with the proviso that $R_1$ together with $R_2$, and/or $R_3$ together with $R_4$ form a bivalent cyclic group with at least 5 ring atoms whereby the two free valencies are linked to $M_1$ or $M_2$, respectively.

Catalytic compositions employing the bidentate ligands used in this method in which $M_1$ and $M_2$ are phosphorous are also presented.

12 Claims, No Drawings

CARBONYLATION PROCESS

BACKGROUND OF THE INVENTION

This invention relates to a process for the carbonylation of ethylenically unsaturated compounds by reaction with carbon monoxide and a co-reactant in the presence of a palladium-containing catalyst system.

EP-A-495547 describes reactions in which optionally substituted olefinically unsaturated compounds are reacted with carbon monoxide and a co-reactant in the presence of a catalyst system comprising a source of palladium-cations, a source of specific aliphatic bidentate diphosphines and a source of anions. A variety of products are also described in the patent. These products are produced in accordance with disclosed carbonylation reactions depending upon the reactants, the prevailing reaction conditions and the selected catalyst system. The relative amounts of co-reactants, the composition of the diphosphine ligand and on the source of anions also greatly enhances or suppresses the production of these varying products.

For example, when an olefin is reacted with carbon monoxide and with an alcohol as co-reactant, the reaction product will be an ester. If an acid is selected as co-reactant, the reaction product will comprise an anhydride group. With ammonia, or a primary or secondary amine as co-reactant, an amide group-containing product will be obtained. The use of water as co-reactant will result in the formation of a carboxylic acid, while polarizable molecular hydrogen will react to form aldehydes and/or alcohols.

The catalyst system in that patent uses an aliphatic diphosphine ligand, $Q_1Q_2PXPQ_3Q_4$), the groups $Q_1$, $Q_2$, $Q_3$, and $Q_4$, or one or both pairs of $Q_1$ and $Q_2$, and $Q_3$ and $Q_4$, preferably are unsubstituted, optionally branched or cyclic alkyl or alkylene groups having from 1 to 10 carbon atoms. These catalyst systems comprise, in addition to palladium cations and a diphosphine ligand, a source of anions. As anion source, Protonic acid are the preferred anion sources. Most notable among these acids are those which are sources of non-coordinating or weakly-coordinating anions, i.e. anions which do not or only weakly coordinate with the palladium cation. Thus, a particularly preferred source of anions is a strong acid having a pKa of less than 3.5. If the anions are derived from a weak acid, e.g. a carboxylic acid, the carboxylic acid is preferably sterically hindered. Bulky substituents on these weak acids will minimize the tendency for coordination.

While one skilled in the art can generally obtain desired products in reasonably good yields based on the teachings of EP-A-495547, reaction rates have been found to be disappointingly low. Of course, this greatly effects the commercial viability of these reactions. Accordingly, improving the reaction rates of carbonylation reactions without impeding such factors as selectivity and catalyst stability continues to be a highly sought goal.

SUMMARY OF THE INVENTION

It is an object of this invention to provide a process for the carbonylation of ethylenically unsaturated compounds by the reaction of carbon monoxide and a co-reactant.

It is a further object of this invention to provide a carbonylation reaction of ethylenically unsaturated compounds with an improved rate of reaction over prior art processes employing palladium catalyst systems.

It is a yet further object of this invention to provide a process for the carbonylation of ethylenically unsaturated compounds in a substantially nonacidic environment.

It is a yet further object of this invention to provide a catalyst system for the carbonylation of ethylenically unsaturated compounds by the reaction of carbon monoxide and a co-reactant.

In accordance with this invention, a process is provided for the carbonylation of ethylenically unsaturated compounds by reaction with carbon monoxide and a co-reactant in the presence of a substantially non-acidic catalyst.

The catalyst system comprises a source of palladium and a bidentate ligand of the formula $R_1R_2M_1RM_2R_3R_4$ (Formula I). In this ligand, $M_1$ and $M_2$ independently may be phosphorus, arsenic, or antimony atoms.

R is a bivalent organic bridging group and $R_1$, $R_2$, $R_3$ and $R_4$ are unsubstituted or substituted aliphatic groups. Further, one or more combinations of $R_1$, $R_2$, $R_3$, and $R_4$ occur to form a bivalent cyclic group. These cyclic groups have at least 5 ring atoms in which the two free valencies are linked to $M_1$ or $M_2$. The combinations include $R_3$ together with $R_4$, $R_1$ together with $R_2$, and $R_1$ together with $R_2$ and $R_3$ together with $R_4$.

Catalysts used according this process are also presented in this invention.

DETAILED DESCRIPTION OF THE INVENTION

Surprisingly, it has now been found that by using a substantially non-acidic catalyst system and by selecting a specific category of bidentate ligands, the rate of a number of carbonylation reactions is significantly increased over what had been known in the art.

It is believed that the carbonylation reactions according to the invention proceed under the influence of an active catalyst system containing palladium cations in complex coordination with a bidentate ligand.

The palladium cations may originate from salts. For example, salts derived from nitric acid have been found useful in this regard. Additionally, sulfuric acid, and sulfonic acids, such as p-toluenesulfonic acid, methanesulfonic acid or trifluoromethanesulfonic acid can be used as palladium cation sources. Preferably, a palladium salt of a carboxylic acid is used such as acetic acid, trifluoroacetic acid, or propionic acid.

It is also possible to employ a palladium source such as the metallic element itself or a zero valence palladium complex. Such a zero valence complex can be used with carbon monoxide, for example. However, this would require the presence of a protonic acid. It will be appreciated that the amount of protonic acid used has to be selected very carefully so that the catalyst system remains substantially nonacidic.

In the bidentate ligands of formula (I), both $M_1$ and $M_2$ preferably represent phosphorus atoms. R preferably represents a bivalent organic bridging group, containing from 1 to 10 atoms in the bridge. More preferably, R represents an alkylene group containing from 1 to 4 atoms in the bridge. In general the bridging group consists of carbon and hydrogen atoms only, but it may also comprise a carbon chain, interrupted by a heteroatom, such as an oxygen atom. A most preferred embodiment of formula (I) employs an ethylene group as R.

The cyclic groups formed by $R_1$ together with $R_2$ and/or $R_3$ together with $R_4$ have at least 5 ring atoms. More preferred embodiments have 6 to 9 ring atoms. Ring systems having 7 or 8 carbon atoms are even more preferred. These ring atoms are generally carbon atoms but cyclic groups containing 1 or 2 heteroatoms in the ring such as oxygen or nitrogen atoms are not precluded. The two free valencies may occur at adjacent carbon ring atoms or at two carbon atoms which are further apart. Examples of suitable cyclic groups include but are not limited to: 1,2-cyclooctylene, 1,3-cyclooctylene, 1,4-cyclooctylene, 1,5-cyclooctylene, 1,4-cyclohexylene, 1,3-cycloheptylene and 1,4-cycloheptylene groups.

Mixtures of bidentate ligands may also be used. Here, $R_1$ together with $R_2$ may represent various cyclic groups while $R_3$ and $R_4$ represent either non-cyclic aliphatic groups. Alternatively, $R_3$ together with $R_4$ may represent cyclic groups which may be the same as or different from the cyclic group represented by $R_1$ and $R_2$. Examples of suitable mixtures of bidentate ligands are 1,2-bis(9-phosphabicyclo[3.3.1.]nonyl)ethane and 1,2-bis(9-phosphabicyclo[4.2.1.]nonyl)ethane; 1,3-bis(9-phosphabicyclo[3.3.1.]nonyl)propane and 1,3-bis(9-phosphabicyclo[4.2.1.]nonyl)propane; 1-dialkylphosphino-2-P-(9-phosphabicyclo[3.3.1]nonyl)ethane and 1-dialkylphosphino-2-P-(9-phosphabicyclo[4.2.1.-]nonyl)ethane.

In embodiments in which $R_1$ and $R_2$, or $R_3$ and $R_4$ do not represent a bivalent cyclic group, they can be optionally substituted alkyl or monovalent cycloalkyl groups. $C_{1-6}$ alkyls and $C_{5-10}$ cycloalkyls are preferred. Examples of suitable alkyl groups are methyl, ethyl or butyl groups. Cyclohexyl or cyclooctyl groups are preferred cycloalkyls.

The ratio of number of moles of ligands of formula (I) per gram atom of palladium is preferably in the range of from 0.5 to 10. The most preferred range is from 1 to 3 moles of ligand per gram atom of palladium.

The process according to the invention is preferably carried out in the presence of a basic compound. Without being bound to theory, it is believed that the presence of a basic compound not only ensures that the catalyst system remains non-acidic during the process, but also favorably affects the catalytic activity. Accordingly, it is considered likely, that at least part of the quantity of basic compound participates in the catalyst system. Nitrogen bases have been found to be preferred with nitrogen-containing compounds wherein the nitrogen atoms are only linked to atoms other than hydrogen being most preferred. Examples of suitable nitrogen bases are trialkylamines, preferably tri-$C_{1-6}$ alkylamines, especially triethylamine, tripropylamine, tri-n-butylamine and tri-tert-butylamine. Examples of suitable cyclic amines that are also useful in this regard include pyridine and alkylpyridines. $C_{1-4}$ pyridines such as 2-methylpyridine, 3,4-dimethylpyridine and 1,10-phenanthroline are the most preferred cyclic amines.

The amount of basic compound is not critical and may vary between wide limits. Usually a molar amount of basic compound is selected in the range of from 1 to 100. A preferred range of basic compound is from 1 to 20 moles of basic compound per gram atom of palladium.

Conveniently, the amount of catalyst system used in this invention is relatively small. Preferred amounts are in the range of $10^{-7}$ to $10^{-1}$ gram atom palladium per mole of ethylenically unsaturated compound. A more preferred range is from $10^{-6}$ to $10^{-2}$ gram atom of palladium per mole of unsaturated compound.

Catalyst compositions comprising a palladium compound, a bidentate ligand of the formula $R_1R_2PRPR_3R_4$ wherein R is a bivalent organic bridging group containing from 1 to 10 atoms in the bridge and $R_1$, $R_2$, $R_3$ and $R_4$ independently represent substituted or non-substituted aliphatic groups, with the proviso that $R_1$ together with $R_2$ and/or $R_3$ together with $R_4$ represent a bivalent cyclic group with at least 6 ring atoms, whereby the two free valencies are linked to the phosphorus atoms, and a basic compound, are novel. Accordingly, the invention also relates to these catalyst compositions.

Preferred embodiments of these catalysts comprise a palladium compound and a bidentate ligand in which $R_1R_2P$ and $R_3R_4P$ each represent a 9-phosphabicyclo[3.3.1.]nonyl- or a 9-phosphabicyclo[4.2.1.]nonyl group and R represents an ethylene group, and the basic compound is a pyridine or a trialkylamine.

The bidentate ligands may be prepared by known techniques such as those described in British Patent Specification No. 1,127,965.

The ethylenically unsaturated compound referred to throughout this specification may have one or more double bonds. Preferably, they are olefins having from 2 to 20 carbon atoms per molecule. The unsaturated bonds may be internal or, preferably, terminal. $C_{2-8}$ such as ethene, propene, butene-1, hexene-1 and octene-1 are particularly preferred.

The ethylenically unsaturated compounds may have one or more hydrogen atoms substituted by other atoms such as halogen atoms. They may also be substituted by functional groups such as hydroxyl groups, cyano groups, methoxy groups, ethoxy groups, and amino groups such as dimethyl- and diethyl-amino groups.

Another preferred category of ethylenically unsaturated compounds consists of unsaturated esters of carboxylic acids and esters of unsaturated carboxylic acids. For example, the starting material may be a vinyl ester of a carboxylic acid such as acetic acid or propionic acid, or it may be an alkyl ester of an unsaturated acid, such as the methyl or ethyl ester of acrylic acid or methacrylic acid.

Suitable co-reactants in the process of the invention include compounds comprising a nucleophilic moiety and a mobile hydrogen atom. Examples are mono- and dihydric alkanols. Methanol, ethanol, n-butanol, ethylene glycol, isopropanol, butanediols and hexanol-1, and amines, such as ethylamine and diethylamine are also examples of such moieties. $C_{1-6}$ alkanols and $C_{2-6}$ alkanediols are preferred. n-Butanol-1, methanol and 1,4-butanediol are especially preferred as co-reactants. These co-reactants enable the production of valuable carbonylation products such as methylpropionate, butylpropionate and 1,4-diacyloxy butanes which are of considerable commercial interest given their use in solvents and in flavoring compositions and perfumes.

In the process of this invention, the ethylenically unsaturated compound or the co-reactant may be used in excess and may accordingly serve as a solvent during the reaction. It is also possible to perform the reaction in the presence of an additional liquid diluent. This is particularly the case when the reactants are used in stoichiometric amounts. Suitable diluents are, for example, polar aprotic compounds such as ketones or ethers.

Preferred diluents are tetrahydrofuran and the dimethylether of diethyleneglycol (diglyme).

Further reaction promoters, such as drying agents, may also be used in the process of this invention. Suitable drying agents include acetals, such as dimethylacetal of acetone, ketals and the like. A preferred drying agent is trimethyl orthoformate.

The carbonylation reaction may be carried out at moderate temperatures. Generally, a range between 30° and 200° C. is used. A preferred range is from 50° to 150° C. Reaction pressures may be atmospheric or superatmospheric. In particular pressures in the range of from 5 to 70 bar are preferred. Higher pressures are not precluded but usually do not provide advantages.

The invention will be illustrated by the following nonlimiting examples.

EXAMPLES I-XI

The experiments were carried out by each time charging a 250 mL magnetically-stirred "HASTELLOY C" (A Trade Mark of the Hastelloy Company) autoclave with 0.25 mmol palladium (II)acetate, 0.6 mmol of a diphosphine ligand, 50 mL of an alkanol co-reactant and, where applicable, one or more additives. The autoclave was flushed with a 1.5:1 molar mixture of carbon monoxide and ethene and pressurized to a total pressure of 50 bar. The autoclave was then sealed and the mixture was heated to the desired reaction temperature.

The reaction was continued to complete ethene conversion and subsequently the reaction mixture was cooled to room temperature and the pressure released. The ligand, co-reactant, additive (if any), reaction temperature and average hourly rate of ester formation are shown in Table 1.

The abbreviations used in the table have the following meanings:

BPBNP = 1,3-bis(9-phospha-bicyclononyl)propane
BPBNE = 1,2-bis(9-phospha-bicyclononyl)ethane
DMP = 3,4-dimethylpyridine(lutidine)
Phen = 1,10-phenanthroline
BBA = 2,6-di(sec.butoxy)benzoic acid
TEA = triethylamine
TMF = trimethyl orthoformate The product obtained in Example V was methylpropionate; in the other examples n-butylpropionate was obtained. The selectivity with respect to the ester was more than 99%.

From the results of Examples I, II and III it can be seen that by the presence of a basic compound, the rate is increased and that a further increase in rate is obtained by adding a drying agent. Likewise, comparing the results of Examples IV, VI, VII and VIII, an increase in rate is observed by adding a drying agent or a basic compound. The effect of adding a drying agent is further illustrated by comparing the results of Examples IX and X.

TABLE 1

| Example | Ligand | Additive (mmol) | Alkanol (mL) | Temperature (°C.) | Rate (mol/gat Pd.h) |
|---|---|---|---|---|---|
| I | BPBNP | — | n-butanol 50 | 125 | 35 |
| II | " | DMP 10 | n-butanol 50 | 137 | 85 |
| III | " | " TMF 5 mL | n-butanol 50 | 137 | 330 |
| IV | BPBNE | — | n-butanol 50 | 125 | 520 |
| V | " | — | methanol 50 | 125 | 490 |
| VI | " | TMF 1 mL | n-butanol 50 | 125 | 600 |
| VII | " | Phen 1 | n-butanol 50 | 125 | 630 |
| VIII | " | Phen 2.5 TMF 1 mL | n-butanol 50 | 125 | 1150 |
| A* | " | BBA 10 | n-butanol 50 | 120 | 360 |
| IX | " | TEA 10 | n-butanol 50 | 133 | 275 |
| X | " | " TMF 5 mL | n-butanol 50 | 133 | 725 |
| XI | " | DMP 10 TMF 5 mL | n-butanol 50 | 135 | 1160 |

*not according to the invention, for comparison only

EXAMPLE B—Comparative Example

An experiment was carried out, substantially under the conditions as described for Example IV with the differences that the reaction temperature was 130° C., instead of 125° C. and that as ligand 1,2-bis(dicyclohexylphosphino)ethane was used. The rate was 30 mol/gat Pd.h.

This example shows that the reaction rate of prior art methods and catalysts is far slower than those attained by the processes and catalysts of the instant invention.

EXAMPLE C—Comparative Example

An experiment was carried out, substantially under the conditions as described for Example II, with the difference that as ligand 1,3-bis(di-sec.butylphosphino)-propane was used. The rate was 50 mol/gat Pd.h/

This example shows that the reaction rate of prior art methods and catalysts is far slower than those attained by the processes an catalysts of the instant invention.

EXAMPLE XII

An experiment was carried out, whereby the autoclave was charged with 0.25 mmol palladium (II) acetate, 0.6 mmol of a diphosphine ligand (BPBNP as defined above), 10 mmol of triethylamine, 5 mL of trimethyl orthoformate, 50 mL of methanol and 20 mL of n-octene-1. The autoclave was flushed and pressurized with carbon monoxide to a pressure of 30 bar. The mixture was heated to 130° C. The reaction was continued to complete octene conversion and subsequently the reaction mixture was cooled to room temperature and the pressure released.

The reaction rate was 100 mol/gat Pd.h. The linearity of the formed methyl ester of nonanoic acid was 73%.

EXAMPLE XIII

An experiment was carried out, substantially as described in Example XII, with the difference that instead of BPBNP as ligand BPBNE was used. (BPBNP and BPBNE are as defined above). The rate was 170 mol/gat Pd.h. The linearity of the formed methyl ester of nonanoic acid was 69%.

What is claimed is:

1. A process for the carbonylation of ethylenically unsaturated compounds by reaction with carbon monoxide and a correactant in the presence of a substantially non-acidic catalyst system;
said catalyst system comprising:
a) a source of palladium;
b) a bidentate ligand of the formula $R_1R_2M_1RM_2R_3R_4$
wherein $M_1$ and $M_2$ independently are selected from the group consisting of phosphorous, arsenic, and antimony;
R is a bivalent organic bridging group;
$R_1$, $R_2$, $R_3$, and $R_4$ are selected from the group consisting of substituted and non-substituted aliphatic groups;
further wherein a cycloalkylene group with at least 5 ring atoms linked to $M_1$ or $M_2$ is formed from the members of the group consisting of $R_3$ together with $R_4$, $R_1$ together with $R_2$, and $R_1$ together with $R_2$ and $R_3$ together with $R_4$; and
c) a base.

2. The process of claim 1 wherein said source of palladium is a salt of a palladium carboxylic acid compound.

3. The process of claim 1 wherein $M_1$ and $M_2$ are phosphorus atoms.

4. The process of claim 1 wherein the bridging group R comprises between 1 and 10 atoms in the bridge.

5. The process of claim 4 wherein R is an alkylene group comprising between 1 and 4 atoms in the bridge.

6. The process of claim 5 wherein R is an ethylene group.

7. The process of claim 1 wherein said cycloalkylene group contains between 6 and 9 ring atoms.

8. The process of claim 7 wherein R is linked to two phosphorus atoms, each of which participates in a member of the group consisting of 9-phosphabicyclo[3.3.1.]nonyl- and a 9-phosphabicyclo[4.2.1.]nonyl group.

9. The process of claim 8 wherein said base is selected from the group consisting of substituted and unsubstituted pyridines.

10. The process of claim 8 wherein said base is a trialkylamine.

11. The process of claim 8 wherein said base comprises between 1 and 100 moles per gram atom of palladium.

12. The process of claim 1 wherein said cycloalkenes are selected from the group consisting of 9-phosphabicyclo[3.3.1.]nonyl- and 9-phosphabicyclo[4.2.1.]nonylgroup and said base is selected from the group consisting of alkyl pyridines and trialkylamines.

* * * * *